United States Patent [19]

Inuzuka et al.

[11] 3,959,075

[45] May 25, 1976

[54] PROCESS FOR THE PRODUCTION OF L-LYSINE

[75] Inventors: Keiichi Inuzuka; Shinichiro Hamada, both of Hofu, Japan

[73] Assignee: Kyowa Hakko Kogyo Co., Ltd., Tokyo, Japan

[22] Filed: July 15, 1975

[21] Appl. No.: 595,999

[30] Foreign Application Priority Data
July 17, 1974  Japan.................................. 49-81142

[52] U.S. Cl................................ 195/29; 195/28 R; 195/47; 195/111
[51] Int. Cl.² ......................................... C12D 13/06
[58] Field of Search.............. 195/28 R, 29, 30, 47, 195/111

[56] References Cited
UNITED STATES PATENTS
3,888,737   6/1975   Watanabe et al. ................ 195/28 R

*Primary Examiner*—A. Louis Monacell
*Assistant Examiner*—Robert J. Warden
*Attorney, Agent, or Firm*—Fitzpatrick, Cella, Harper & Scinto

[57] ABSTRACT

L-lysine is produced in enhanced yields by culturing an L-lysine-producing microorganism in a nutrient medium supplemented by the culture liquor of an L-leucine-producing microorganism.

11 Claims, No Drawings

PROCESS FOR THE PRODUCTION OF L-LYSINE

BACKGROUND OF THE INVENTION

This invention relates to a process for producing L-lysine in enhanced yields by fermentation. More specifically, this invention relates to a process for producing L-lysine in enhanced yields which comprises culturing an L-lysine-producing microorganism in a nutrient medium supplemented by the culture liquor of an L-leucine-producing microorganism.

L-lysine is well known as one of the essential amino acids for human and animal nutrition and is in great demand as a food and animal feed supplement.

Heretofore, there has been known a variety of processes for the fermentative production of L-lysine. The typical of those processes comprise the use of L-lysine-producing mutants of coryneform glutamic acid-producing bacteria represented by *Corynebacterium glutamicum*.

Coryneform glutamic acid-producing bacteria are clearly defined in the art. They are generally characterized by being ellipsoidal spheres to short rods, Gram-positive, non-sporulating and non-motile, requiring biotin and accumulating large amounts of L-glutamic acid.

Numbers of coryneform glutamic acid-producing bacteria have been already reported. They are classified depending upon the opinion of taxonomists who conducted studies on the bacteria, to the species: *Corynebacterium glutamicum*, *Brevibacterium aminogenes*, *Brevibacterium divaricatum*, *Brevibacterium flavum*, *Brevibacterium lactofermentum*, *Brevibacterium roseum*, *Brevibacterium saccharolyticum*, *Brevibacterium immariophilium*, *Corynebacterium acetoacidophilum*, *Corynebacterium herculis*, *Corynebacterium lilium*, *Corynebacterium callunae*, *Microbacterium ammoniaphilum* and *Arthrobacter* species.

However, they are taxonomically very closely related with each other as described by Abe et al in J. General and Applied Microbiology, Vol. 13, 279–301 (1967). Coryneform glutamic acid-producing bacteria are represented by *Corynebacteium glutamicum*.

L-lysine-producing mutants of coryneform glutamic acid-producing bacteria are generally characterized by having at least one of the two properties resulted from gene mutation.

One of the two properties is the complete or incomplete blockage of biosynthetic pathway for the production of related amino acids. This property is recognized as a requirement for related amino acids such as L-homoserine, L-threonine, L-methionine, L-leucine, L-isoleucine, etc. or as a sensitivity to L-threonine or L-methionine. The other property is the complete or incomplete deviation from the feedback regulations by related amino acids. This property is recognized as a resistance to related amino acids such as L-lysine, L-threonine, etc. or their analogs such as S-(2-aminoethyl)-L-cysteine, etc.

The productivity of L-lysine by the L-lysineproducing mutants having the above properties is improved by combining further genetical mutations other than those described above, for example, requirements for amino acids such as L-valine, L-tyrosine, etc., vitamins such as thiamin, vitamin $B_{12}$, etc. and purine bases such as adenine, guanine, etc.

Further, the productivity of L-lysine is also improved by combining genetical mutations other than those described above, for example, resistances to amino acids such as L-isoleucine, their analogs such as 2-amino-3-methylthiobutyric acid, etc. and antibiotics such as penicillin G, polymixin B, etc.

Preferred L-lysine-producing mutants include:
*Micrococcus glutamicus* ATCC 13286, ATCC 13287,
*Brevibacterium flavum* ATCC 21475, ATCC 21127.
ATCC 21128, ATCC 21517, ATCC 21518, ATCC 21528
ATCC 21529, and
*Corynebacterium glutamicum* ATCC 21299, ATCC 21300,
ATCC 21513, ATCC 21514, ATCC 21515, ATCC 21516,
ATCC 21527, ATCC 21544, KY 10403, KY 10031. Most of the above-mentioned specific mutants are described in U.S. Pat. Nos. 2,979,439, 3,616,218, 3,687,810, 3,707,441, 3,708,395 and U.K. Pat. No. 1,186,988.

In producing L-lysine by culturing L-lysine-producing strains such as described above, these strains are cultured aerobically in a medium containing an assimilable carbon source, a nitrogen source, inorganic materials and other nutrients.

While studying the production of L-lysine by using an L-lysine-producing strain having a requirement for L-leucine, the present inventors used a culture liquor of an L-leucine-producing mutant as a supplement to the medium in order to satisfy the requirement for L-leucine. As the result, it was unexpectedly found that the productivity of L-lysine by the L-lysine-producing strain was remarkably increased. Further, it was found that the effect is much superior to that where free L-leucine is added to the medium in an amount corresponding to that contained in the culture liquor of the L-leucine-producing mutant.

Furthermore, it was found that the effect of the addition of the culture liquor of the L-leucine-producing mutant was obtained not only when the L-lysine-producing strain having a requirement for L-leucine but also always when L-lysine-producing strain having various properties are used.

The fermentative production of L-leucine has also been well known in the art. As in the case with the L-lysine-producing mutants, such L-leucine-producing mutants generally have at least one property selected from a requirement for related amino acids including L-isoleucine, L-methionine and L-valine and a resistance to related amino acids including L-leucine and their analogs such as α-aminobutyric acid etc. resulted from the complete or incomplete blockage of biosynthetic pathway and the complete or incomplete deviation from the feedback regulations. The productivity of L-leucine is improved by combining properties other than those described above, for example, requirement for amino acids such as L-phenylalanine, etc. Further the productivity is also improved by combining resistances to amino acids such as L-lysine, L-histidine, etc. and their analogs such as S-(2-aminoethyl)-L-cysteine, 2-thiazolealanine, etc.

Preferred L-leucine-producing mutants include:
*Brevibacterium flavum* (FERM-P No. 1838) ATCC 21889,
*Brevibacterium lactofermentum* (FERM-P No. 1837) ATCC 21888,
*Corynebacterium glutamicum* ATCC 21301-21308, ATCC 21885, ATCC 21886 (FERM-P No. 1835), and

*Corynebacterium acetoacidophilum* (FERM-P No. 1836) ATCC 21887.

Some of the above-mentioned specific strains are described in Japanese Unexamined Patent Application Published under No. 101589/74.

According to the present invention, the yields of L-lysine are greatly improved by culturing L-lysine-producing mutants in a medium supplemented by the culture liquor of L-leucine-producing mutants. This mechanism has not been clarified yet. It has already been well known to improve the productivity of L-lysine by the addition of various amino acids. As described above, the effect of the addition of the culture liquor of L-leucine-producing mutants has been found not due to L-leucine contained in the culture liquor. Although the culture liquor of L-leucine-producing mutants contain various amino acids other than L-leucine, the effect of the addition of the culture liquor has also been found not attributable to such amino acids as described in detail hereinbelow.

Further, the effect of the addition of the culture liquor of L-leucine-producing mutants is characteristic to itself and such effect is not found when the culture liquor of L-glutamic acid-producing microorganisms is used.

DESCRIPTION OF THE INVENTION

In accordance with the present invention, L-lysine is produced in enhanced yields by culturing an L-lysine-producing mutant of coryneform glutamic acid producing bacteria in a nutrient medium supplemented by the culture liquor obtained by culturing an L-leucine-producing mutant of coryneform glutamic acid-producing bacteria.

In the present invention, any L-lysine-producing mutant of coryneform glutamic acid-producing bacteria, having the above-described properties can be used for the production of L-lysine.

Either a synthetic medium or natural medium may be used in the present invention for the culturing of the L-lysine-producing mutant so long as it properly contains an assimilable carbon source, a nitrogen source, inorganic materials and other growth promoting factors which may be required by the specific strains used.

As the carbon source, carbohydrates such as glucose, fructose, sorbitol, mannitol, glycerol, starch, starch hydrolyzate, etc., molasses, blackstrap molasses, etc., organic acids such as acetic acid, fumaric acid, lactic acid, pyruvic acid, succinic acid, etc. and alcohols such as methanol, ethanol, etc. may be used depending upon the utilization by the microorganisms.

Practically, molasses, blackstrap molasses, acetic acid and glucose are preferred as the carbon source.

As the nitrogen source, ammonia, organic and inorganic ammonium salts such as ammonium chloride, ammonium sulfate, ammonium carbonate, ammonium acetate, ammonium phosphate, etc., nitrogen-containing compounds such as urea etc., peptone, meat extract, yeast extract, corn steep liquor, casein hydrolyzate, fish meal, digested fish meal, defatted soybean, digested defatted soybean, acid hydrolyzate of soybean protein, etc. may used.

Additionally, as inorganic materials, potassium dihydrogen phosphate, dipotassium hydrogen phosphate, magnesium sulfate, sodium chloride, ferrous sulfate, manganese sulfate, calcium carbonate, etc. may be used.

Further, when the L-lysine-producing mutants have a nutritional requirement for amino acids, vitamins, purine bases, etc., an appropriate amount of such nutrients must, of course, be supplemented to the medium. For example, coryneform glutamic acid-producing bacteria and, therefore, the L-lysine-producing mutants thereof require biotin for growth. Accordingly it is necessary that an appropriate amount of biotin is present in the medium. It is to be understood that if the required nutrients are contained in other constituents of the medium, it is not necessary to specifically supplement the sources of the nutrients to the medium.

According to the present invention, the addition of the culture liquor obtained by culturing the L-leucine-producing mutant to the L-lysine fermentation medium is effective to enhance the yields of L-lysine. Such culture liquor to be added to the L-lysine fermentation medium may be employed either as is or after removal of the microbial cells. In either case, it is, of course, necessary to sterilize the culture liquor or culture filtrate prior to use.

Those skilled in the art will appreciate that the amount of culture liquor of an L-leucine-producing mutant which is used to supplement the nutrient medium for the L-lysine production may vary according to the microorganisms and the compositions of media employed both in L-lysine production and in L-leucine production. However, it is preferred that the L-lysine fermentation medium contains the culture liquor at a concentration of 2 to 150 ml/l based on the volume of the nutrient medium for L-lysine fermentation, the optimum amount being readily determined for each particular application.

In adding the culture liquor of an L-leucine-producing mutant, all the amount to be added may be present in the initial medium. It is also possible to add a portion to the initial medium and to supplement the remaining portion during the culturing. Alternatively, all the amount to be added may be supplemented during the culturing.

When the culture liquor is added during the culturing, the culture liquor may be fed all at one time, intermittently or continuously to the L-lysine fermentation medium. In this case, in order to obtain the desired effect of the addition of the culture liquor of the L-leucineproducing mutant, it is perferable that the feeding is completed up to the end of the logarithmic propagation stage of the microorganism. Generally, the logarithmic propagation stage is over in 10 to 24 hours from the start of the culturing.

Fermentation of L-lysine producing mutant is carried out under the conditions normally employed in L-lysine fermentation, that is, under aerobic conditions, for example, with aeration and stirring or with shaking at a temperature of 25° to 40°C and a pH of 6 to 8.5. Usually, after 30 to 150 hours of culturing, a considerable amount of L-lysine is accumulated in the culture liquor.

After the completion of culturing, L-lysine is isolated and purified by any of the methods well known in the art, such as an ion exchange resin treatment, crystallization by concentration and the like.

The culture liquor of the L-leucine-producing mutant, which is effective to provide enhanced yields of L-lysine according to the present invention, may be prepared by the conventional methods for the production of L-leucine. Any L-leucine-producing mutant of coryneform glutamic acidproducing bacteria having the above-described properties may be used in the present invention to produce the culture liquor.

Like in the case with L-lysine fermentation, either a synthetic medium or a natural medium may be used in L-leucine fermentation so long as it properly contains an assimilable carbon source, a nitrogen source, inorganic materials and other nutrients necessary for the growth of the microorganisms to be employed. As regards the specific carbon sources, nitrogen sources and inorganic materials, those mentioned in connection with L-lysine fermentation are also useful for L-leucine fermentation. Molasses, blackstrap molasses, acetic acid and glucose are mentioned as preferred carbon sources from the practical standpoint. It is needless to say that when the specific strains to be used require nutrients, such nutrients must, of course, be present in the medium.

Culturing of L-leucine-producing mutant is carried out under the conventional culturing conditions. Generally, culturing is carried out under aerobic conditions, for example, with aeration and stirring or with shaking at a temperature of 25° to 40°C and a pH of 6 to 9 for 48 to 120 hours.

The following experimental examples are illustrative of the determination of a preferred range of the amount of the culture liquor of the L-leucine-producing mutant to be added to the L-lysine fermentation medium.

EXPERIMENTAL EXAMPLE 1

A basal medium having the following composition is prepared.

| | | |
|---|---|---|
| glucose | 150 | g/l |
| $(NH_4)_2SO_4$ | 40 | g/l |
| $KH_2PO_4$ | 1 | g/l |
| $MgSO_4.7H_2O$ | 0.4 | g/l |
| $FeSO_4.7H_2O$ | 0.01 | g/l |
| $MnSO_4.4H_2O$ | 6 | mg/l |
| biotin | 300 | γ/l |
| thiamine HCl | 200 | γ/l |
| Ajieki* | 1 | g/l |
| $CaCO_3$ | 5 | g/l |
| L-threonine | 600 | γ/ml |
| DL-methionine | 200 | γ/ml |
| (pH 7.4 before sterilization) | | |

*A trade name for acid hydrolyzate of soybean protein available from Ajinomoto Inc., Japan.

6 kinds of media are prepared by adding a culture liquor of L-leucine-producing strain containing 15.6 g/l of L-leucine to the basal medium in different amounts shown in Table 1 below.

*Brevibacterium flavum* ATCC 21518 is inoculated into 10 ml portions of the basal medium as well as the thus prepared 6 kinds of the media in 250 ml-Erlenmeyer flasks and cultured at 28°C for 110 hours with shaking. After the completion of culturing, the yields of L-lysine and the growth of the cells are determined. The results are shown in Table 1 below.

Table 1

| Concentration of the culture liquor of L-leucine-producing strain added (ml/l) | Yield of L-lysine (g/l) | Growth of the cells (g/l dry cells) |
|---|---|---|
| 0 | 2 | 9.8 |
| 2 | 40 | 10.9 |
| 5 | 48 | 12.5 |
| 10 | 55 | 13.8 |
| 20 | 60 | 15.3 |
| 40 | 59 | 14.7 |

Table 1-continued

| Concentration of the culture liquor of L-leucine-producing strain added (ml/l) | Yield of L-lysine (g/l) | Growth of the cells (g/l dry cells) |
|---|---|---|
| 60 | 56 | 13.5 |

The culture liquor of L-leucine-producing strain is prepared in the following manner:

*Corynebacterium glutamicum* (FERM-P No. 1834) ATCC 21885 is inoculated into 3 l of a seed medium having the following composition in a 5 l-jar fermenter.

| | | |
|---|---|---|
| D-glucose | 50 | g/l |
| peptone | 10 | g/l |
| yeast extract | 10 | g/l |
| corn steep liquor | 5 | g/l |
| sodium chloride | 2.5 | g/l |
| urea | 3 | g/l |
| biotin | 50 | γ/l |
| (pH 7.2 before sterilization) | | |

Culturing is carried out at 30°C for 18 hours with aeration of 3 l/min. and stirring at 600 r.p.m.

1 l of the seed culture is inoculated into 10 l of a main fermentation medium having the following composition in a 30 l-jar fermenter.

| | | |
|---|---|---|
| ammonium acetate | 5.0 | g/l |
| $KH_2PO_4$ | 2.0 | g/l |
| $MgSO_4.7H_2O$ | 0.5 | g/l |
| $FeSO_4.7H_2O$ | 0.1 | g/l |
| $MnSO_4.4H_2O$ | 0.01 | g/l |
| biotin | 50 | γ/l |
| thiamine HCl | 100 | mg/l |
| (pH 7.4 before sterilization) | | |

Culturing is carried out at 30°C for 60 hours with aeration of 10 l/min. and stirring at 400 r.p.m.

After 3 hours from the start of culturing, 10 l of a mixture containing 71 g/l of ammonium acetate and 380 g/l of acetic acid is continuously fed to the medium for a period of 56 hours so that the pH of the medium is maintained at 6.8 and the concentration of acetic acid in the medium is maintained at 1.2 - 18 g/l. After the completion of culturing, 15.6 g/l of L-leucine is accumulated in the culture liquor.

EXPERIMENTAL EXAMPLE 2

*Corynebacterium glutamicum* ATCC 21516 is used as the L-lysine-producing strain and is cultured in the same manner as described in Experimental Example 1 above, except for using the culture liquor of L-leucine-producing strain in different amounts shown in Table 2 below.

Table 2

| Concentration of the culture liquor of L-leucine-producing strain added (ml/l) | Yield of L-lysine (g/l) | Growth of the cells (g/l dry cells) |
|---|---|---|
| 0 | 30 | 9.0 |
| 2 | 37 | 10.1 |
| 5 | 48 | 12.6 |
| 10 | 56 | 13.5 |
| 20 | 62 | 14.9 |
| 40 | 58 | 14.4 |
| 60 | 55 | 14.0 |
| 80 | 53 | 13.8 |

Table 2-continued

| Concentration of the culture liquor of L-leucine-producing strain added (ml/l) | Yield of L-lysine (g/l) | Growth of the cells (g/l dry cells) |
| --- | --- | --- |
| 100 | 54 | 13.3 |
| 150 | 52 | 13.5 |

Now, the present invention is further illustrated by the following representative examples.

EXAMPLE 1

In this example, *Corynebacterium glutamicum* ATCC 21513 (an L-lysine-producing strain) is inoculated into 330 ml of a seed medium having the following composition in a 2 l-Erlenmeyer flask and is cultured at 28°C for 24 hours with shaking.

Composition of the seed medium:

| | | |
| --- | --- | --- |
| D-glucose | 40 | g/l |
| $KH_2PO_4$ | 0.5 | g/l |
| $K_2HPO_4$ | 1.5 | g/l |
| urea | 3 | g/l |
| $MgSO_4 \cdot 7H_2O$ | 0.5 | g/l |
| peptone | 20 | g/l |
| meat extract | 5 | g/l |
| biotin | 50 | γ/l |
| (pH 7.2 before sterilization ps | | |

5 kinds of media having the following compositions, respectively, are prepared Medium A-1:

| | | |
| --- | --- | --- |
| blackstrap molasses | 150 | g/l (as glucose) |
| $MgSO_4 \cdot 7H_2O$ | 0.3 | g/l |
| $KH_2PO_4$ | 0.7 | g/l |
| urea | 3 | g/l |
| Ajieki | 20 | g/l |
| (pH 7.4 before sterilization) | | |

Medium A-2:
  Medium A-1
  +
  13 ml/l of culture liquor of an L-leucineproducing strain (containing 15.0 g/l of
  L-leucine)

Medium A-3:
  Medium A-1
  +
  200 mg/l of L-leucine

Medium A-4:
  Medium A-1
  +
  13 ml/l of culture liquor of an L-glutamic acidproducing strain (containing 60 g/l of L-gluatmic acid)

Medium A-5:
  Medium A-1
  +
  13 ml/l of the culture liquor of an L-glutamic acid-producing strain used to prepare Medium A-4.
  +
  200 mg/l of L-leucine.

1 l of the seed culture prepared above is inoculated into 10 l portions of the above-mentioned 5 kinds of media in 30 l-jar fermenters. Culturing is carried out at 28°C for 48 hours with aeration of 10 l/min. and stirring at 400 r.p.m. During the culturing the pH of the medium is maintained at 6.8 with 22% aqueous ammonia.

After the completion of culturing, the resulting culture liquors contain L-lysine shown in Table 3.

Table 3

| Medium | Additive | Yield of L-lysine (g/l) |
| --- | --- | --- |
| A-1 | none | 40 |
| A-2 | Culture liquor of L-leucine-producing strain | 55 |
| A-3 | L-leucine | 44 |
| A-4 | Culture liquor of L-glutamic acid-producing strain | 40 |
| A-5 | Culture liquor of L-glutamic acid-producing strain + L-leucine | 46 |

The culture liquor of the L-leucine-producing strain and that of the L-glutamic acid-producing strain employed above are prepared in the following manners, respectively.

Preparation of the culture liquor of the L-leucine-producing strain

*Brevibacterium lactofermentum* (FERM-P No. 1837) ATCC 21888 (an L-leucine-producing strain) is inoculated into 3 l of a seed medium having the following composition in a 5 l-jar fermenter and cultured at 30°C for 18 hours with aeration of 3 l/min. and stirring at 600 r.p.m. Composition of the seed medium:

| | | |
| --- | --- | --- |
| D-glucose | 50 | g/l |
| peptone | 10 | g/l |
| yeast extract | 10 | g/l |
| corn steep liquor | 5 | g/l |
| NaCl | 2.5 | g/l |
| urea | 3 | g/l |
| biotin | 50 | γ/l |
| (pH 7.2 before sterilization) | | |

1 l of the thus prepared seed culture is inoculated into 10 l of a main fermentation medium having the following composition in a 30 l-jar fermenter. Composition of the main fermentation medium:

| | | |
| --- | --- | --- |
| ammonium acetate | 15 | g/l |
| $KH_2PO_4$ | 2.0 | g/l |
| $MgSO_4 \cdot 7H_2O$ | 0.5 | g/l |
| $FeSO_4 \cdot 7H_2O$ | 0.1 | g/l |
| $MnSO_4 \cdot 4H_2O$ | 0.01 | g/l |
| biotin | 50 | γ/l |
| thiamine HCl | 100 | mg/l |
| (pH 7.4 before sterilization) | | |

Culturing is carried out at 30°C for 60 hours with aeration of 10 l/min. and stirring at 400 r.p.m. while maintaining the pH of the medium at around 6.8 with 60% aqueous acetic acid solution. After 7 hours from the start of culturing, 70 ml portions of an aqueous solution containing 11 g of ammonium acetate are fed to the medium every one hour for 50 times. During the culturing, the concentration of acetic acid in the medium is maintained at 1.2 - 18 g/l. After the completion of culturing, 15.0 g/l of L-leucine is accumulated in the culture liquor.

Preparation of the culture liquor of the L-glutamic acidproducing strain

*Arthrobacter paraffineus* ATCC 15591 (an L-glutamic acid-producing strain) is inoculated into 300 ml of a seed medium having the following composition in a 2 l-Erlenmeyer flask and cultured at 30°C for 24 hours with shaking. Composition of the seed medium:

| | | |
| --- | --- | --- |
| sodium acetate | 10 | g/l |
| peptone | 10 | g/l |
| meat extract | 5 | g/l |
| NaCl | 2.5 | g/l |

-continued
(pH 7.0 before sterilization)

300 ml of the thus prepared seed culture is inoculated into 3 l of a main fermentation medium having the following composition in a 5 l-jar fermenter. Composition of the main fermentation medium:

| | | |
|---|---|---|
| ammonium acetate | 20 | g/l (as acetic acid) |
| KH$_2$PO$_4$ | 1 | g/l |
| K$_2$HPO$_4$ | 1 | g/l |
| MgSO$_4$.7H$_2$O | 0.5 | g/l |
| MnSO$_4$.4H$_2$O | 10 | mg/l |
| FeSO$_4$.7H$_2$O | 10 | mg/l |
| thiamine HCl | 5 | γ/l |

(pH 7.0 before sterilization)

Culturing is carried out at 30°C for 3 days with aeration of 3 l/min. and stirring at 600 r.p.m. During the culturing, 1 l of an aqueous solution obtained by adding 3 parts by weight of water to the mixture of 70 parts by weight of glacial acetic acid and 27 parts by weight of 22% aqueous ammonia is fed to the medium, while maintaining the pH of the medium at 4 - 9. The feeding is completed two hours prior to the completion of culturing. After the completion of culturing, 60 g/l of L-glutamic acid is accumulated in the culture liquor.

The Medium A-2 employed above, comprising Medium A-1 and the culture liquor obtained by culturing the L-leucine-producing strain, contains amino acids originated from the culture liquor, Ajieki and blackstrap molasses, respectively in amounts shown below.

| | Amounts of amino acid (mg/l) | | |
|---|---|---|---|
| Amino acid | Originated from the culture liquor of L-leucine-producing strain | Originated from Ajieki | Originated from blackstrap molasses |
| alanine | 6.37 | 176 | 99.0 |
| aspartic acid | — | 967 | 278 |
| arginine | — | 546 | 7.5 (as hydrochloride) |
| cystine | — | — | 3.0 |
| glycine | 4.81 | 332 | 7.5 |
| glutamic acid | 12.6 | 1570 | 9.0 |
| histidine | — | 242 | 13.5 (as hydrochloride) |
| isoleucine | 5.85 | 284 | — |
| leucine | 195 | 586 | — |
| lysine | 5.2 | 550 | — |
| methionine | — | 98 | — |
| phenylalanine | — | 340 | 12.0 |
| proline | — | 460 | — |
| serine | — | 376 | 52.5 |
| threonine | — | 362 | 52.5 |
| tryptophan | — | — | 7.5 |
| tyrosine | — | 208 | 13.5 |
| valine | — | 310 | 48 |

From the above, it is apparent that the amounts of amino acids originated from the culture liquor of the L-leucineproducing strain are very small as compared to those of amino acids originated from Ajieki or blackstrap molasses. Thus, it can be understood that the amino acids originated from the culture liquor of the L-leucine-producing mutant do not give any additional effects on the production of L-lysine. In view of the above, it is concluded that the effect of the addition of the culture liquor of the L-leucine-producing strain is not attributable to that of the amino acids contained in the culture liquor.

EXAMPLE 2

In this example, 4 kinds of media having the following compositions, respectively, are prepared. Medium B-1:

| | | |
|---|---|---|
| D-glucose | 150 | g/l |
| (NH$_4$)$_2$SO$_4$ | 40 | g/l |
| KH$_2$PO$_4$ | 1 | g/l |
| MgSO$_4$.7H$_2$O | 0.4 | g/l |
| FeSO$_4$.7H$_2$O | 0.01 | g/l |
| MnSO$_4$.4H$_2$O | 6 | mg/l |
| biotin | 300 | γ/l |
| thiamine HCl | 200 | γ/l |
| Ajieki | 1 | g/l |
| CaCO$_3$ | 5 | g/l |
| L-threonine | 600 | γ/ml |
| DL-methionine | 200 | γ/ml |

(pH 7.4 before sterilization)

Medium B-2:
  Medium B-1
  +
  20 ml/l of culture liquor of an L-leucineproducing strain (containing 15.6 g/l of L-leucine) prepared in Experimental Example 1

Medium B-3:
  Medium B-1 +
  320 mg/l of L-leucine

Medium B-4:
  Medium B-1 +
  1 g/l of Ajieki

Brevibacterium flavum ATCC 21518 (an L-lysine-producing strain) is inoculated into 10 ml portions of the above-described four kinds of media in 250 ml-Erlenmeyer flasks and cultured at 80°C for 110 hours with shaking.

After the completion of culturing, the resulting culture liquors contain L-lysine shown in Table 4.

Table 4

| Medium | Additive | Yield of L-lysine (mg/l) |
|---|---|---|
| B-1 | none | 32 |
| B-2 | Culture liquor of L-leucine-producing strain | 60 |
| B-3 | L-leucine | 35 |
| B-4 | Ajieki | 46 |

EXAMPLE 3

In this example, Corynebacterium glutamicum ATCC 21516, Brevibacterium flavum ATCC 21528, Corynebacterium glutamicum ATCC 21544 and Corynebacterium glutamicum KY 10013 (all of which are L-lysine-producing strains) are used. These strains are separately inoculated into 40 ml of a seed medium having the following composition in 250 ml-Erlenmeyer flasks and are cultured at 28°C for 24 hours with shaking. Composition of the seed medium:

| | | |
|---|---|---|
| D-glucose | 50 | g/l |
| NaCl | 2.5 | g/l |
| urea | 3 | g/l |
| peptone | 10 | g/l |
| yeast extract | 10 | g/l |
| corn steep liquor | 5 | g/l |
| biotin | 50 | γ/l |

(pH 7.2 before sterilization)

3 kinds of media having the following compositions, respectively, are prepared.
Medium C-1:

| | | |
|---|---|---|
| blackstrap molasses | 100 | g/l (as glucose) |
| KH$_2$PO$_4$ | 0.5 | g/l |
| MgSO$_4$ (anhydride) | 0.5 | g/l |
| (NH$_4$)$_2$SO$_4$ | 3.3 | g/l |
| Ajieki | 20 | g/l |
| (pH 7.4 before sterilization) | | |

Medium C-2:
  Medium C-1 +
  20 ml/l of the culture liquor of the L-leucine-producing strain prepared in Example 1 (containing 15.0 g/l of L-leucine)
Medium C-3:
  Medium C-1 +
  300 mg/l of L-leucine Table 5

| Strain | Medium | Additive | Yield of L-lysine (g/l) |
|---|---|---|---|
| | C-1 | none | 27.0 |
| Corynebacterium glutamicum ATCC 21516 | C-2 | Culture liquor of L-leucine-producing strain | 32.0 |
| | C-3 | L-leucine | 27.2 |
| | C-1 | none | 26.1 |
| Brevibacterium flavum ATCC 21528 | C-2 | Culture liquor of L-leucine-producing strain | 28.7 |
| | C-3 | L-leucine | 26.0 |
| | C-1 | none | 27.8 |
| Corynebacterium glutamicum ATCC 21544 | C-2 | Culture liquor of L-leucine-producing strain | 30.5 |
| | C-3 | L-leucine | 26.8 |
| | C-1 | none | 23.0 |
| Corynebacterium glutamicum KY 10013 | C-2 | Culture liquor of L-leucine-producing strain | 25.0 |
| | C-3 | L-leucine | 22.9 |

EXAMPLE 4

In this example, Corynebacterium glutamicum KY 10403 (an L-lysine-producing strain) is seed cultured in the same manner as described in Example 1.

3 kinds of media having the following compositions, respectively, are prepared. Medium D-1:

| | | |
|---|---|---|
| blackstrap molasses | 150 | g/l (as glucose) |
| MgSO$_4$.7H$_2$O | 0.3 | g/l |
| KH$_2$PO$_4$ | 0.7 | g/l |
| urea | 3 | g/l |
| Ajieki | 10 | g/l |
| (pH 7.4 before sterilization) | | |

Medium D-2:
  Medium D-1 +
  20 ml/l of the culture liquor of the L-leucine-producing strain prepared in Example 1 (containing 15.0 g/l of L-leucine)
Medium D-3:
  Medium D-1 +
  300 mg/*l* of L-leucine 1 l of the seed culture is inoculated into 10 l portions of the above-mentioned 3 kinds of media in 30 l-jar fermenters and cultured in the same manner as described in Example 1.

After the completion of culturing, the resulting culture liquors contain L-lysine shown in Table 6.

Table 6

| Medium | Additive | Yield of L-lysine (g/l) |
|---|---|---|
| D-1 | none | 41 |

Table 6-continued

| Medium | Additive | Yield of L-lysine (g/l) |
|---|---|---|
| D-2 | Culture liquor of L-leucine-producing strain | 52 |
| D-3 | L-leucine | 45 |

EXAMPLE 5

In this example, Corynebacterium glutamicum ATCC 21513 (an L-lysine-producing strain) is seed cultured in the same manner as described in Example 1.

3 kinds of media having the following compositions, respectively, are prepared.
Medium E-1:
  The same composition as Medium A-1 described in Example 1.
Medium E-2:
  Medium E-1 +
  13 ml/l of culture liquor of an L-leucine-producing strain (containing 15.8 g/l of L-leucine)
Medium E-3:
  Medium E-1 +
  200 mg/l of L-leucine 1 l of the seed culture is inoculated into 10 l portions of the above-mentioned 3 kinds of media in 30 l-jar fermenters. Culturing is carried out at 28°C for 48 hours with aeration of 10 l/min. and stirring at 400 r.p.m. During the culturing, the pH of the medium is maintained at 6.8 with 22% aqueous ammonia.

After the completion of culturing, the resulting culture liquors contain L-lysine shown in Table 7.

Table 7

| Medium | Additive | Yield of L-lysine (g/l) |
|---|---|---|
| E-1 | none | 41 |
| E-2 | Culture liquor of L-leucine-producing strain | 57 |
| E-3 | L-leucine | 46 |

The culture liquor of the L-leucine-producing strain employed above is prepared in the following manner.

Brevibacterium lactofermentum (FERM-P No. 1837) ATCC 21888 (an L-leucine producing strain) is seed cultured in the same manner as described in Example 1. 1 l of the seed culture is inoculated into 10 l of a main fermentation medium having the following composition in a 30 l-jar fermenter. Composition of the main fermentation medium:

| | | |
|---|---|---|
| blackstrap molasses | 150 | g/l (as glucose) |
| MgSO$_4$.7H$_2$O | 0.3 | g/l |
| KH$_2$PO$_4$ | 0.7 | g/l |
| (NH$_4$)$_2$SO$_4$ | 20 | g/l |

Culturing is carried out at 30°C for 30 hours with aeration of 10 l/min. and stirring at 400 r.p.m. while maintaining the pH of the medium at 6.8 with 22% aqeuous ammonia. After the completion of culturing, 15.8 g/*l* of L-leucine is accumulated in the culture liquor.

EXAMPLE 6

In this example, Corynebacterium glutamicum ATCC 21513 (an L-lysine-producing strain) is seed cultured in the same manner as described in Example 1.

3 kinds of madia having the following compositions, respectively, are prepared. Medium F-1:

| ammonium acetate | 15 | g/l |
| --- | --- | --- |
| $KH_2PO_4$ | 2.0 | g/l |
| $MgSO_4.7H_2O$ | 0.5 | g/l |
| $FeSO_4.7H_2O$ | 0.1 | g/l |
| $MnSO_4.4H_2O$ | 0.01 | g/l |
| biotin | 50 | γ/l |
| thiamine HCl | 100 | mg/l |
| Ajieki | 20 | g/l |
| (pH 7.4 before sterilization) | | |

Medium F-2:
  Medium F-1 +
  13 ml/l of the culture liquor of L-leucine-producing strain (containing 15.8 g/l of L-leucine) prepared in Example 5.

Medium F-3:
  Medium F-1 +
  200 mg/l of L-leucine 1 l of the seed culture is inoculated into 10 l portions of the above-mentioned 3 kinds of media in 30 l-jar fermenters. Culturing is carried out at 28°C for 62 hours with aeration of 10 l/min. and stirring at 400 r.p.m. while maintaining the pH of the medium at 6.8 with 60% aqueous acetic acid solution. After 10 hours from the start of culturing, 70 ml portions of an aqueous solution containing 13 g of ammonium acetate are fed to the medium every one hour for 50 times. During the culturing, the concentration of acetic acid in the medium is maintained at 0.5 – 15 g/l.

After the completion of culturing, the resulting culture liquors contain L-lysine shown in Table 8.

Table 8

| Medium | Additive | Yield of L-lysine (g/l) |
| --- | --- | --- |
| F-1 | none | 32 |
| F-2 | Culture liquor of L-leucine-producing strain | 48 |
| F-3 | L-leucine | 35 |

EXAMPLE 7

In this example, the procedure described in Example 6 is repeated except that the culture liquor of L-leucine-producing strain prepared in Example 1 is used. The results are shown in Table 9.

Table 9

| Additive | Yield of L-lysine (g/l) |
| --- | --- |
| none | 30 |
| Culture liquor of L-leucine-producing strain | 49 |
| L-leucine | 34 |

What is claimed is:

1. In a process for producing L-lysine by culturing an L-lysine-producing mutant of coryneform glutamic acid-producing bacteria in a nutrient medium, the improvement which comprises culturing said mutant in a first nutrient medium comprising assimilable carbon and nitrogen sources and an effective amount of culture liquor obtained from culturing an L-leucine-producing mutant of coryneform glutamic acid-producing bacteria in a second nutrient medium, and thereafter recovering said L-lysine.

2. A process according to claim 1 wherein from 2 to 150 ml/l of said culture liquor of L-leucine-producing mutant is present in said first medium.

3. A process according to claim 1 wherein said culture liquor of L-leucine-producing mutant is added to said first medium in increments and all of said culture liquor of L-leucine-producing mutant is added up to the end of logarithmic propagation stage.

4. A process according to claim 1 wherein said carbon source is at least one selected from the group consisting of molasses, blackstrap molasses, glucose and acetic acid.

5. A process according to claim 1 wherein said L-lysine-producing mutant belongs to a species selected from the group consisting of *Brevibacterium aminogenes, Brevibacterium divaricatum, Brevibacterium flavum, Brevibacterium lactofermentum, Brevibacterium roseum, Brevibacterium saccharolyticum, Brevibacterium immariophilium, Corynebacterium acetoacidophilum, Corynebacterium glutamicum, Corynebacterium herculis, Corynebacterium lilium, Corynebacterium callunae, Microbacterium ammoniaphilum* and *Arthrobacter* species.

6. A process according to claim 1 wherein said L-leucine-producing mutant belongs to a species selected from the group consisting of *Brevibacterium aminogenes, Brevibacterium divaricatum, Brevibacterium flavum, Brevibacterium lactofermentum, Brevibacterium roseum, Brevibacterium saccharolyticum, Brevibacterium immariophilium, Corynebacterium acetoacidophilum, Corynebacterium glutamicum, Corynebacterium herculis, Corynebacterium lilium, Corynebacterium callunae, Microbacterium ammoniaphilum* and *Arthrobacter* species.

7. A process according to claim 1 wherein culturing of said L-lysine-producing mutant is carried out at a temperature of from 25° to 40°C and at a pH of 6 to 8.5.

8. A process for the production of L-lysine which comprises culturing an L-leucine-producing mutant of coryneform glutamic acid-producing bacteria in a first nutrient medium for 48 to 120 hours to produce a culture liquor, supplementing said culture liquor to a second nutrient medium comprising assimilable sources of carbon and nitrogen, culturing an L-lysine-producing mutant of coryneform glutamic acid-producing bacteria in said second nutrient medium and thereafter recovering L-lysine from said medium.

9. A process according to claim 8 wherein said carbon source is at least one selected from the group consisting of molasses, blackstrap molasses, glucose and acetic acid.

10. A process according to claim 8 wherein said culture liquor of L-leucine-producing mutant is supplemented at a concentration of 2 to 150 ml/l based on the volume of said second nutrient medium.

11. A process according to claim 8 which includes the step of removing microbial cells from said culture liquor prior to the addition thereof to said second nutrient medium.

* * * * *